(12) United States Patent
Takagi

(10) Patent No.: US 11,950,985 B2
(45) Date of Patent: Apr. 9, 2024

(54) CONNECTABLE DISPOSABLE WEAR ARTICLE AND METHOD OF DETECTING STICKING DEFECT OF TARGET SHEET IN MANUFACTURE THEREOF

(71) Applicant: Daio Paper Corporation, Ehime (JP)

(72) Inventor: Yurika Takagi, Ehime (JP)

(73) Assignee: Daio Paper Corporation, Ehime (JP)

( * ) Notice: Subject to any disclaimer, the term of this patent is extended or adjusted under 35 U.S.C. 154(b) by 431 days.

(21) Appl. No.: 17/283,132

(22) PCT Filed: Nov. 8, 2019

(86) PCT No.: PCT/JP2019/043854
§ 371 (c)(1),
(2) Date: Apr. 6, 2021

(87) PCT Pub. No.: WO2020/100736
PCT Pub. Date: May 22, 2020

(65) Prior Publication Data
US 2021/0386595 A1 Dec. 16, 2021

(30) Foreign Application Priority Data
Nov. 16, 2018 (JP) .................. 2018-215158

(51) Int. Cl.
*A61F 13/15* (2006.01)
*A61F 13/49* (2006.01)
(Continued)

(52) U.S. Cl.
CPC .. *A61F 13/15772* (2013.01); *A61F 13/49007* (2013.01); *A61F 13/51496* (2013.01);
(Continued)

(58) Field of Classification Search
CPC .... A61F 2013/1578; A61F 2013/15796; A61F 13/15585; B32B 38/1833; B32B 2041/04; B32B 2555/02
See application file for complete search history.

(56) References Cited

U.S. PATENT DOCUMENTS 7,935,296 B2 * 5/2011 Koele ................. G21K 5/04
264/410
10,272,000 B2 * 4/2019 Arora ................. B32B 3/266
(Continued)

FOREIGN PATENT DOCUMENTS

CN 107072835 3/2021
JP 2-228962 9/1990
(Continued)

OTHER PUBLICATIONS

International Search Report for PCT/JP2019/043854, dated Feb. 10, 2020.

*Primary Examiner* — Carson Gross
(74) *Attorney, Agent, or Firm* — Andrus Intellectual Property Law, LLP

(57) ABSTRACT

Position detection of a target sheet is facilitated without requiring a register mark. A connectable disposable wear article having a crotch portion M including a center in a front-back direction LD, a ventral side part F extending forward from the center in the front-back direction LD, and a dorsal side part B extending backward from the center in the front-back direction LD, connecting portions 83 to be detachably connected to an outer surface of the ventral side part F being provided on both side portions of the dorsal side part B, a target sheet 20 to which the connecting portions 83 are connected being provided on the outer surface of the ventral side part F, in which a whiteness of all corner
(Continued)

portions 21 on at least one of an inner surface and an outer surface of the target sheet 20 is 80% or more.

3 Claims, 10 Drawing Sheets

(51) Int. Cl.
*A61F 13/514* (2006.01)
*A61F 13/515* (2006.01)
*A61F 13/56* (2006.01)
*A61F 13/84* (2006.01)
*B32B 38/18* (2006.01)
*B32B 41/00* (2006.01)

(52) U.S. Cl.
CPC ........ *A61F 13/515* (2013.01); *A61F 13/5622* (2013.01); *A61F 13/15585* (2013.01); *A61F 2013/1578* (2013.01); *A61F 2013/15796* (2013.01); *A61F 2013/5694* (2013.01); *A61F 2013/8488* (2013.01); *B32B 38/1833* (2013.01); *B32B 2041/04* (2013.01); *B32B 2555/02* (2013.01)

(56) References Cited

U.S. PATENT DOCUMENTS

| | | |
|---|---|---|
| 2003/0169904 A1 | 9/2003 | Koele et al. |
| 2016/0129626 A1 | 5/2016 | Arora et al. |

FOREIGN PATENT DOCUMENTS

| | | |
|---|---|---|
| JP | 11-335960 | 12/1999 |
| JP | 2006-181294 | 7/2006 |
| JP | 2006-305377 | 11/2006 |
| JP | 2008012139 A * | 1/2008 |
| JP | 2015-19724 | 2/2015 |
| JP | 2015507654 A | 3/2015 |
| JP | 2015-223257 | 12/2015 |
| JP | 2016-032607 | 3/2016 |
| JP | 2016-165542 | 9/2016 |
| JP | 2017-533044 | 11/2017 |
| JP | 2017-536874 | 12/2017 |
| JP | 2018-50675 | 4/2018 |
| WO | 2013090370 A1 | 6/2013 |
| WO | 2016/017421 | 2/2016 |

* cited by examiner

[FIG.1]
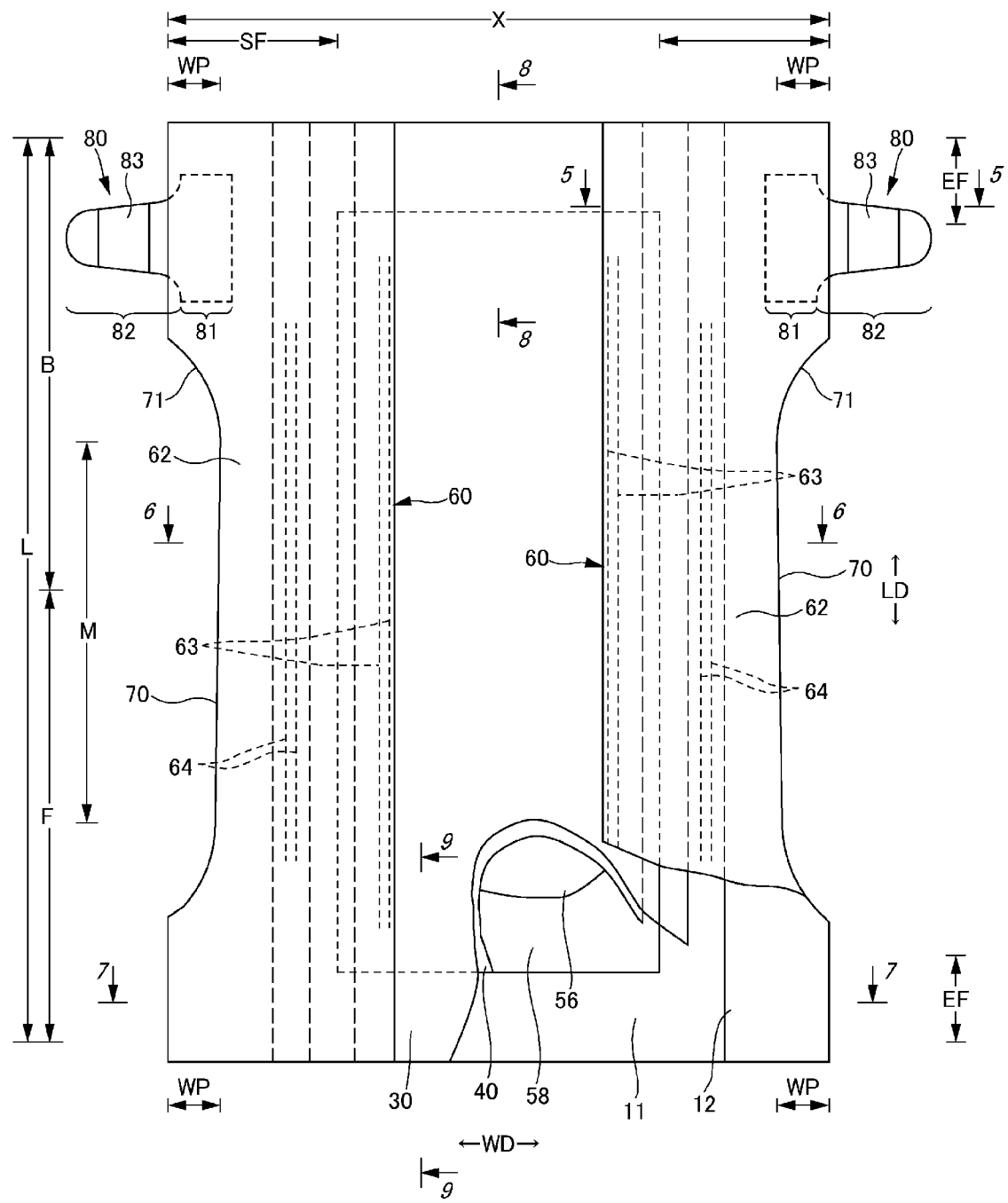

[FIG.2]
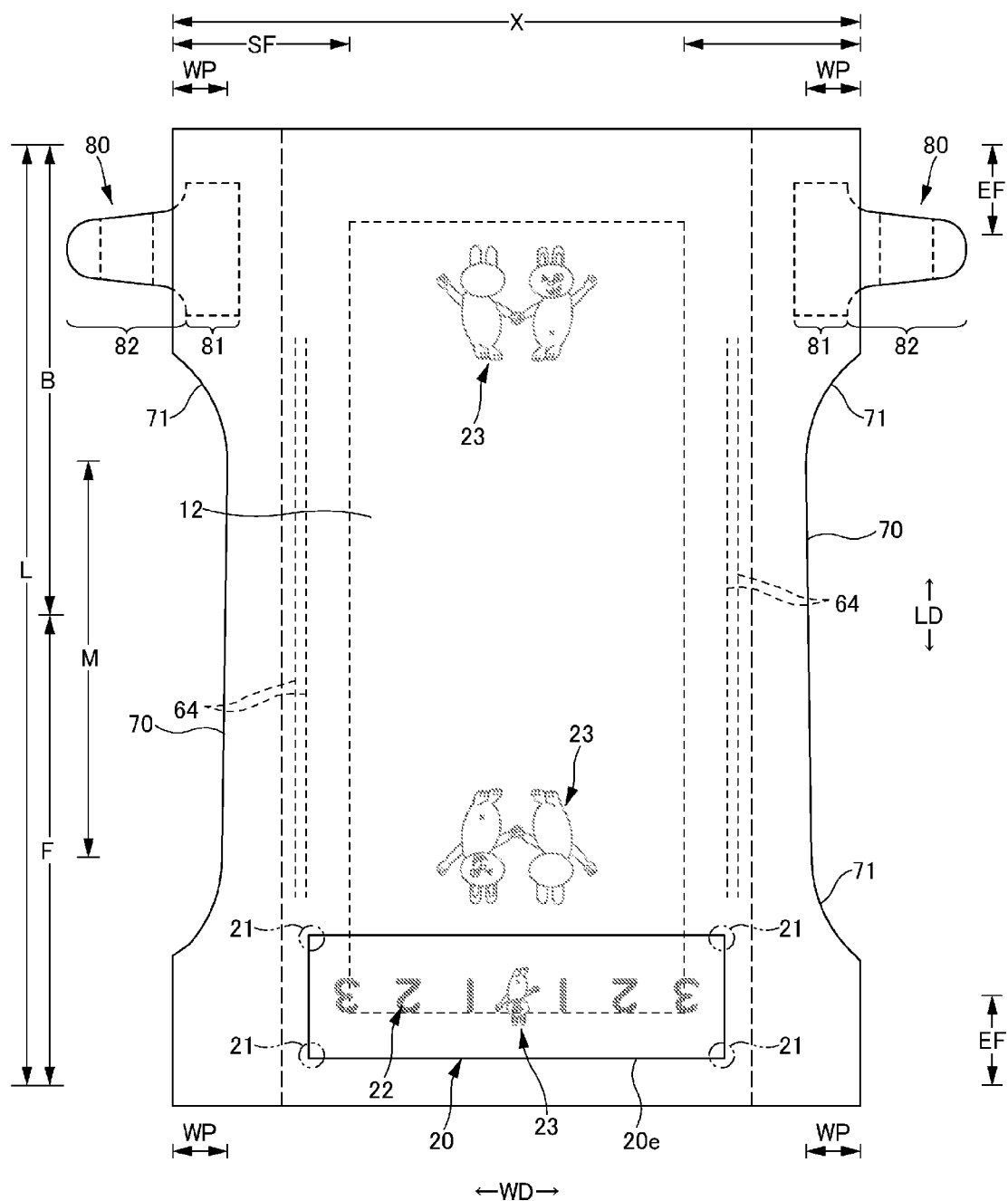

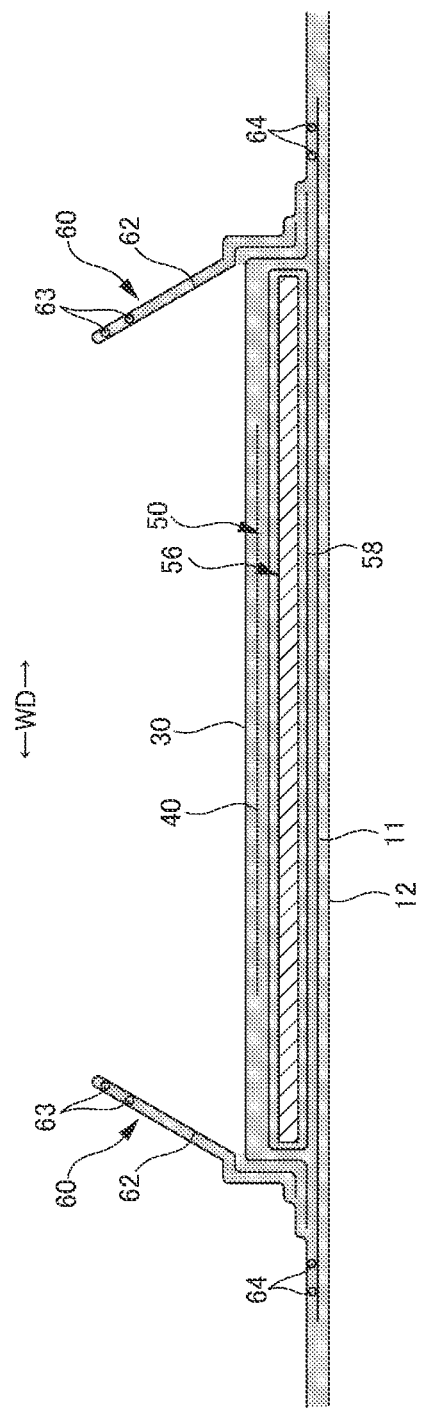

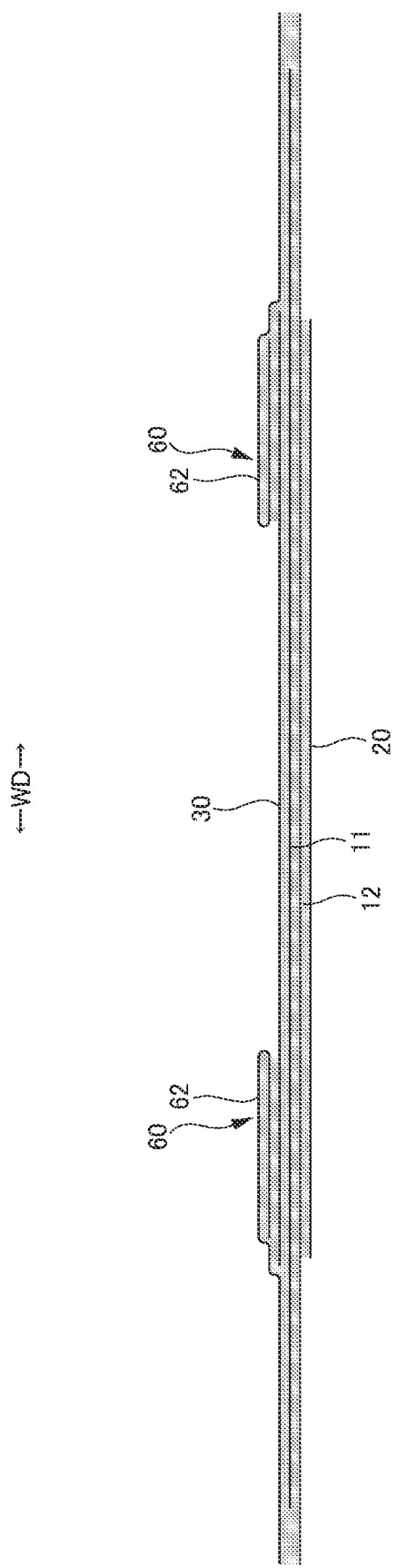

[FIG.5]
(a)
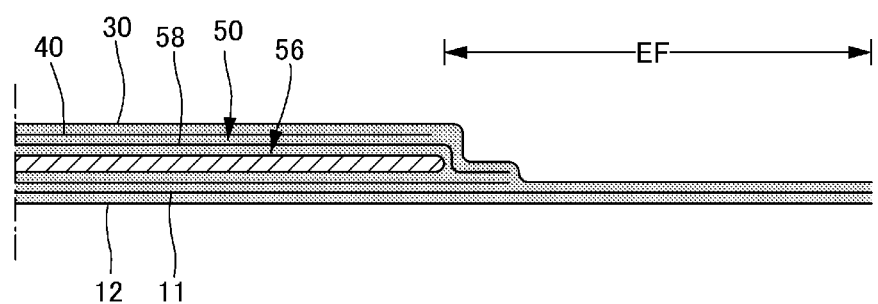
(b)
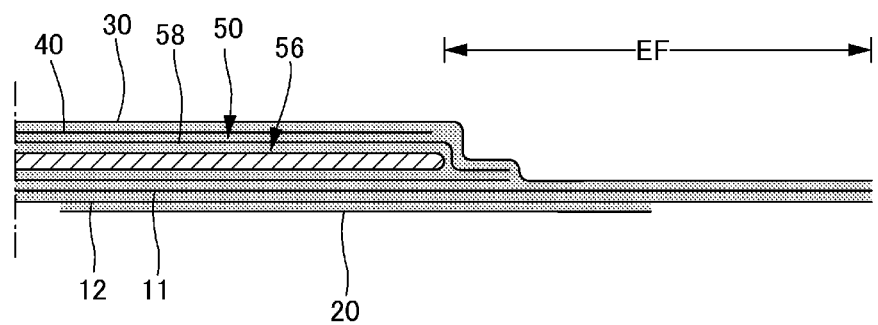

[FIG.6]
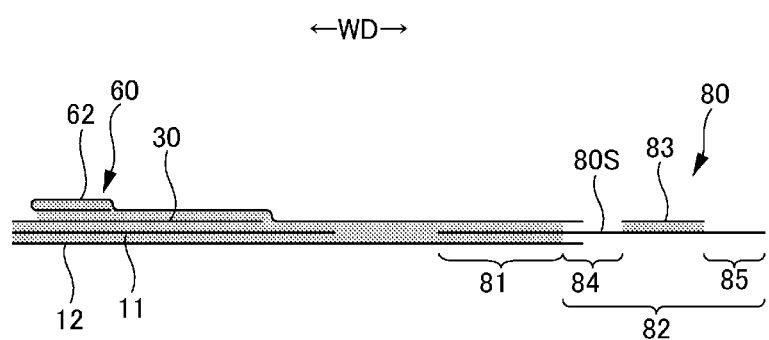

[FIG.7]
(a)
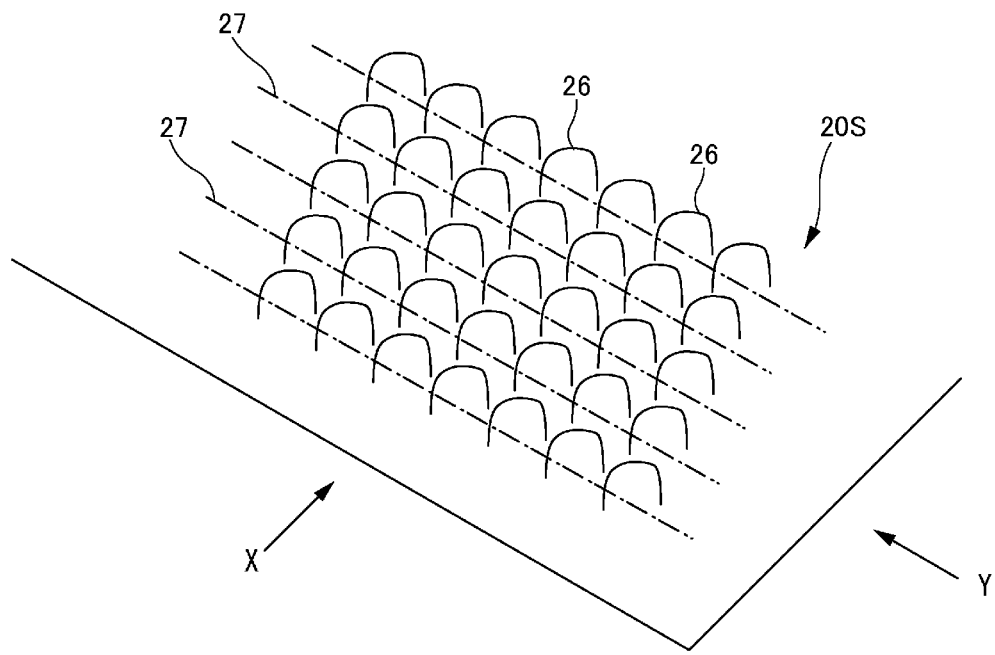
(b)
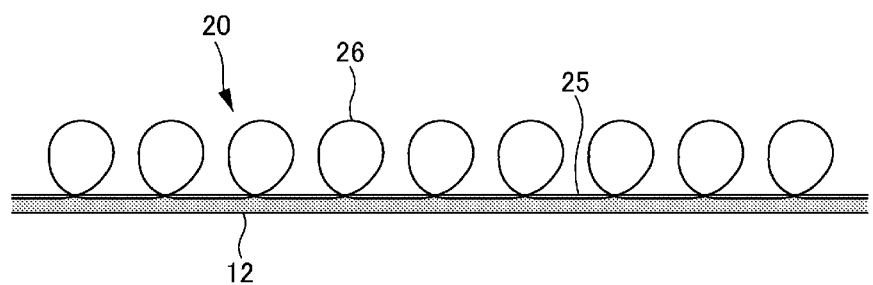
(c)
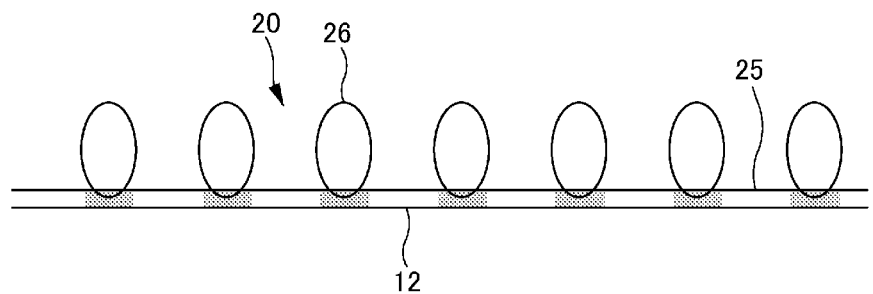

[FIG.8]
(a)
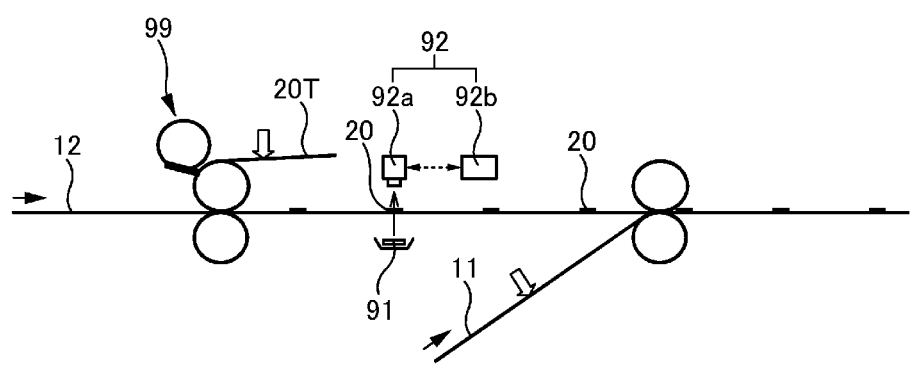
(b)
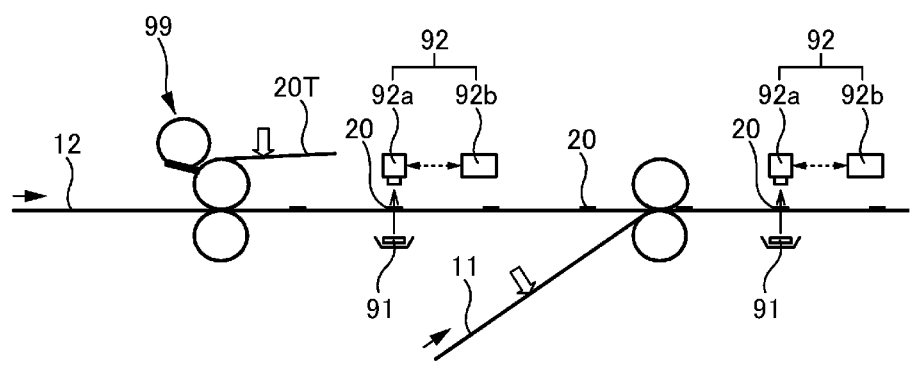

[FIG.9]
(a)
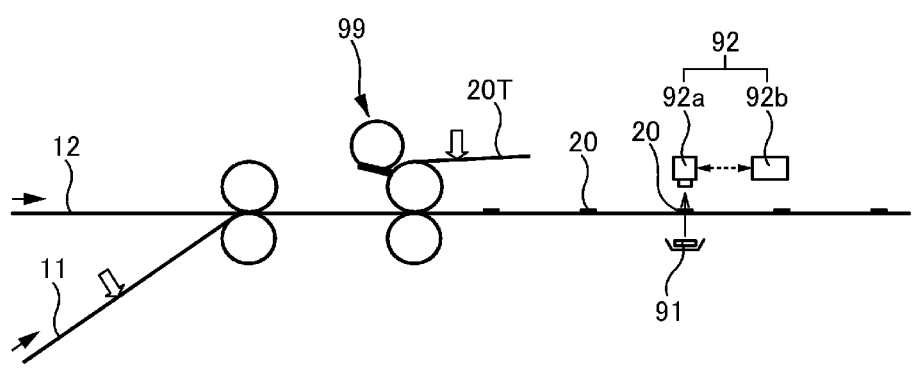
(b)
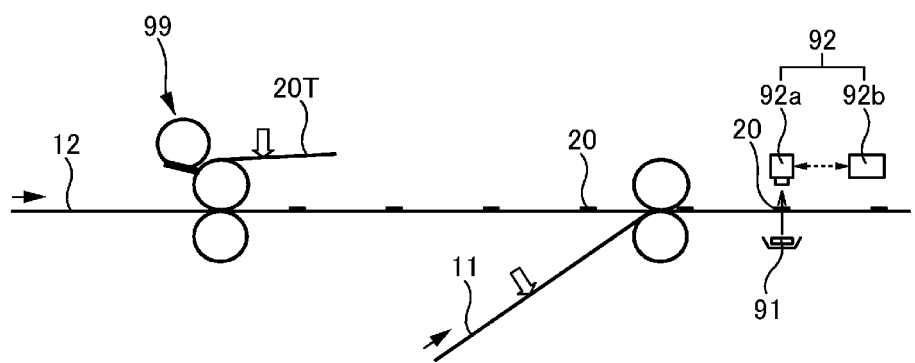

[FIG.10]
(a)
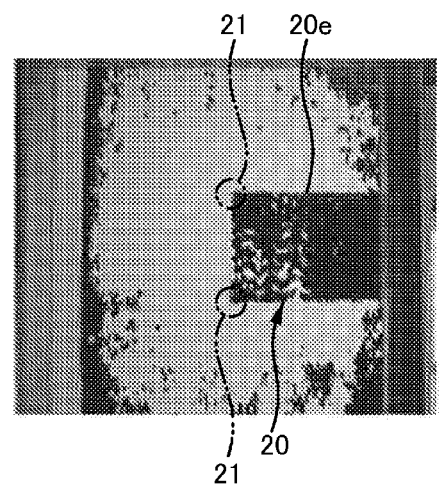
(b)
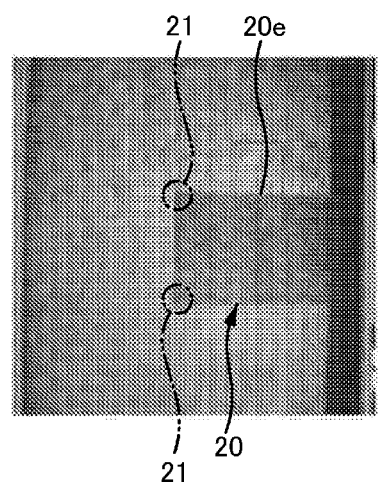

CONNECTABLE DISPOSABLE WEAR ARTICLE AND METHOD OF DETECTING STICKING DEFECT OF TARGET SHEET IN MANUFACTURE THEREOF

CROSS-REFERENCE TO RELATED APPLICATIONS

This application is the U.S. national stage application of International Application PCT/JP2019/043854, filed Nov. 8, 2019, which international application was published on May 22, 2020, as International Publication WO 2020/100736 in the Japanese language. The International Application claims priority of Japanese Patent Application No. 2018-215158, filed Nov. 16, 2018. The international application and Japanese application are both incorporated herein by reference, in entirety.

TECHNICAL FIELD

The present invention relates to a connectable disposable wear article such as a tape-type disposable diaper, and a method of detecting a sticking defect of a target sheet in manufacture thereof.

BACKGROUND ART

A general connectable disposable wear article has a crotch portion including a center in a front-back direction, a ventral side part extending forward from the center in the front-back direction, and a dorsal side part extending backward from the center in the front-back direction, and at least the dorsal side part has wing parts extending both leftward and rightward from the crotch portion in a width direction. In addition, each of the wing parts has a connecting portion that is detachably connected to the outer surface of the ventral side part, and the outer surface of the ventral side part has a sheet-like target sheet to which the connecting portion is connected. During use, the wing parts are turned from both sides of a waist to the outer surface of the ventral side part, and the connecting portions of the wing parts are connected to the target sheet. Such a connectable disposable wear article is used not only for infants but also for nursing care (adult) (for example, see Patent Literature 1).

When such a connectable disposable wear article is continuously manufactured at high speed on a production line, a sticking defect may occur such as curling of corner portions of the target sheet, or shifting of a sticking position. When the target sheet is cut on the production line, deviation of cutting dimensions is included in the sticking defect. Therefore, it is desirable to inspect whether the sticking defect of the target sheet occurs and remove a defective product in the middle of the production line so as not to be mixed in a product package.

In a most common method to detect shapes and dimensions on a production line, a register mark (cash register mark, which is a mark that serves as an index for position detection, and includes all indicators of position detection such as a graphic display for decoration in addition to a simple shape including a rectangle, a line, or a combination thereof) is assigned to a target part (that is, the target sheet in this case) by printing, etc., and the register mark is detected by image recognition from an imaging result of the target part on the manufacturing line, so that the shape of the target part, etc. is detected. For example, when the sticking defect of the target sheet is detected, a border is printed on a part or whole of a peripheral edge including all corners of the target sheet, and this border is used as a register mark, so that it is possible to detect the shape of the target sheet, etc., and to detect curling of the corner portions, etc. based on a detection result.

However, providing the register mark on the target sheet is a restriction on the appearance design. Further, when the register mark is printed on the target sheet, the printing cost increases by the amount of ink used. For example, when there is no print on the target sheet, the cost reduction effect becomes remarkable. However, in that case, it becomes difficult to detect the shape of the target sheet, etc.

CITATION LIST

Patent Literature

Patent Literature 1: JP 2016-165542 A
Patent Literature 2: JP 2016-032607 A

SUMMARY OF INVENTION

Technical Problem

Therefore, a main object of the invention is to facilitate detection of the target sheet without requiring the register mark.

Solution to Problem

A connectable disposable wear article and a method of manufacturing the same solving the above problems are as follows.
<First Aspect>
A connectable disposable wear article having a crotch portion including a center in a front-back direction, a ventral side part extending forward from the center in the front-back direction, and a dorsal side part extending backward from the center in the front-back direction,
  connecting portions to be detachably connected to an outer surface of the ventral side part being provided on both side portions of the dorsal side part,
  a target sheet to which the connecting portions are connected being provided on the outer surface of the ventral side part,
  in which a whiteness of all corner portions on at least one of an inner surface and an outer surface of the target sheet is 80% or more.
(Function and Effect)
The present inventor has examined the following as a method for continuously detecting a target sheet on a production line. That is, in this method, after a target sheet is stuck to an outer surface constituent member of a ventral side part, one of front and back surfaces thereof (for example, opposite side from the target sheet) is irradiated with light, transmitted light transmitted to a surface on the opposite side is detected by a photodetector such as an image sensor, and the target sheet is detected by a difference in light transmittance between a part having the target sheet and the part not having the target sheet. In short, this method utilizes the fact that the light transmittance of a part having high whiteness is lower than that of the surroundings since the part having high whiteness reflects light with all wavelengths. Since most of members of a disposable wear article are thin, are non-colored (white or milky white) in many cases, and have a light transmission property, it has been expected that the target sheet can be detected by such a transmitted light detection method without using a reflected light detection method.

However, when this method was tested, it was found that detecting the target sheet was difficult or possible with lower detection accuracy since the difference in light transmittance between the part having the target sheet and the part not having the target sheet is small.

The disposable wear article is made based on such knowledge. That is, when the whiteness of all the corner portions on at least one of the inner surface and the outer surface of the target sheet is 80% or more, by irradiating the surface of the whiteness with light and detecting light on the opposite surface, light transmittance of all the corner portions of the target sheet is sufficiently reduced, a difference in light transmittance between at least all the corners of the target sheet and an outer part thereof increases, and at least all the corners of the target sheet (that is, a minimum element for recognizing the dimensions and shape of the target sheet) can be detected. For example, when the transmitted light is imaged by the image sensor facing a part including the target sheet, at least all the corner portions of the target sheet appear more distinctly blacker than the outer part thereof. Thus, by recognizing this black part as an image, at least all the corners of the target sheet can be detected. Then, depending on whether the target sheet recognized based on this detection result (for example, detection result of the corners) is normal or not, it is possible to detect sticking defects such as curling of the corner portions of the target sheet, misalignment of a sticking position, and deviation of the cutting dimension when the target sheet is cut on the production line.

In particular, by increasing the whiteness of the target sheet, an influence of the wavelength of light is reduced, so that restrictions on the light source are reduced, and an influence of colors of the members other than the target sheet is reduced.

Note that the outer surface of the target sheet refers to a surface for connecting the connecting portions. The whiteness means "ISO whiteness (diffused blue light reflectance)" specified in JIS P8148:2001. Even though the sample size is specified in the same specification, it is presumed that there is no limitation on the sample size as long as the sample can be measured by a measuring device. In the case of measuring a whiteness of a target sheet, etc. in a product, when a sample having a sufficient size for measurement cannot be obtained, a sample may be prepared using the same material and a whiteness may be measured. As the whiteness measuring device, for example, it is possible to use a spectroscopic white meter PF-10 manufactured by NIPPON DENSHOKU INDUSTRIES CO., LTD.

On the other hand, as far as the present inventor knows, a whiteness of a conventional general target sheet is less than 65%. In such cases, even when the intensity of light from a light source, and sensitivity, aperture, and exposure of a photodetector such as an image sensor are adjusted, or contrast adjustment or contour line enhancement processing is performed by image processing for an imaging result, the effect on the decrease in detection accuracy is unavoidable. The method described in Patent Literature 2 has a common point in that a transmission method is adopted. However, total light transmittance of a target sheet is as high as 60% (that is, a whiteness of the target sheet is low), and contrast to a part other than the target sheet is small. Thus, it is expected that detection of the target sheet will not be easy due to strict conditions and settings.

<Second Aspect>

The connectable disposable wear article according to the first aspect,
in which each of the connecting portions is a hook material of a mechanical fastener, and
the target sheet is a nonwoven fabric in which a constituent fiber has a fineness of 5 to 10 dtex, a basis weight of 20 to 40 g/m$^2$, and a thickness of 0.3 to 0.8 mm and which contains a white pigment.

(Function and Effect)

As the connecting portion of the connectable disposable wear article, a hook material of a mechanical fastener is generally used. In this case, it is preferable to use a nonwoven fabric as the target sheet since a soft touch is obtained. When the target sheet is a nonwoven fabric, the density can be increased in order to increase the whiteness. However, in this case, the hook material of the connecting portion may not be easily entangled. Further, as will be described later, when the displays seen through from the outer surface of the target sheet are printed on the part that overlaps the inside of the target sheet, the displays may be difficult to see through. Therefore, when a nonwoven fabric is used as the target sheet, it is preferable to set a fineness, a basis weight, and a thickness to the above ranges, and make up for the lack of whiteness by adding an appropriate amount of a white pigment such as titanium oxide.

<Third Aspect>

The connectable disposable wear article according to the first or second aspect,
in which a display seen through from the outer surface of the target sheet is printed on a part overlapping an inside of the target sheet, and
a whiteness of the target sheet is 80 to 90%.

(Function and Effect)

When the whiteness of the target sheet is excessively high, in a case where a display seen through from the outer surface of the target sheet is printed on the part that overlaps the inside of the target sheet, the display may be difficult to see. Therefore, the whiteness of the target sheet is preferably within the above range.

<Fourth Aspect>

The connectable disposable wear article according to the third aspect, including
a printing sheet having a first part overlapping the inside of the target sheet and a second part extending around the first part,
in which a target display seen through the outer surface of the target sheet is printed on the first part of the printing sheet,
a display other than the target display is printed on the second part of the printing sheet, and
the target sheet does not have printing.

(Function and Effect)

In many connectable disposable wear articles, a target display such as a scale is printed on the target sheet, and a graphic display such as a pattern or a character is printed around the target sheet. In this case, it is natural that printing on a plurality of members increases the cost. On the other hand, as described above, when printing of the target display and printing of other displays are combined into one printing sheet without performing printing on the target sheet (the target sheet inevitably has no register mark), and the target display is made to be seen through from the outer surface of the target sheet, the cost is significantly reduced, which is preferable.

<Fifth Aspect>

The connectable disposable wear article according to any one of the first to fourth aspects, including an absorber provided at a position including the crotch portion, a liquid pervious top sheet disposed on a front surface side of the absorber, a liquid impervious sheet disposed on a back surface side of the absorber, and an outer nonwoven fabric exposed to the outer surface and disposed on a back surface side of the liquid impervious sheet, wherein the target sheet is stuck to an outer surface of the outer nonwoven fabric, and the outer nonwoven fabric and the liquid impervious sheet have a whiteness of 90% or less on one of an inner surface and an outer surface on the same side as a surface of the target sheet whose whiteness is 80% or more.

(Function and Effect)

In a disposable wear article having a structure of this aspect, it is preferable that the whiteness of the outer nonwoven fabric and the liquid impervious sheet is within the above range. In this way, on the production line, when the target sheet is merely attached to the outer surface of the outer nonwoven fabric (that is, only these two members), or when the liquid impervious sheet is stuck to the inner surface of the outer nonwoven fabric and the target sheet is merely attached to the outer surface (that is, only these two members), the amount of transmitted light is less likely to be insufficient, and the target sheet can be detected with higher accuracy by the above-mentioned transmitted light detection method.

<Sixth Aspect>

A method of detecting a sticking defect of a target sheet in a manufacture of a connectable disposable wear article according to any one of the first to fifth aspects, including sticking the target sheet to an outer surface constituent member of the ventral side part, irradiating a side of the target sheet having a surface whose whiteness is 80% or more with light and detecting transmitted light transmitted to an opposite surface, detecting at least all corners of the target sheet based on a difference in light transmittance between a part having the target sheet and a part not having the target sheet, and detecting a sticking defect of the target sheet depending on whether or not the target sheet recognized based on a detection result is normal.

(Function and Effect)

The same function and effect as those of the cited aspects are achieved.

<Seventh Aspect>

The method of detecting a sticking defect of a target sheet in a manufacture of a connectable disposable wear article according to the sixth aspect, further including imaging the transmitted light by an image sensor facing the opposite surface and acquiring a grayscale image, and detecting at least all corners of the target sheet by recognizing a part of an imaging result having a predetermined gradation or less as an image.

(Function and Effect)

By performing image recognition using a grayscale image in this way, simpler and faster detection processing can be performed. Further, since the whiteness of the target sheet is used, even when a grayscale image is used, there is an advantage that a clearer difference is generated and an influence on the detection accuracy is small.

<Eighth Aspect>

The method of detecting a sticking defect of a target sheet in a manufacture of a connectable disposable wear article according to the sixth or seventh aspect, further including sticking the surface of the target sheet whose whiteness is 80% or more to the outer surface constituent member of the ventral side part, irradiating a surface opposite to a side of the target sheet with light and detecting transmitted light transmitted to a surface on the side of the target sheet.

(Function and Effect)

It is preferable that the light source and the image sensor are disposed according to the present aspect since a contour of the target sheet is less likely to be blurred.

Advantageous Effects of Invention

According to the invention, there is an advantage such as easy detection of the target sheet without requiring a register mark.

BRIEF DESCRIPTION OF DRAWINGS

FIG. 1 is a plan view illustrating an inner surface of a tape-type disposable diaper in a state where the diaper is spread.

FIG. 2 is a plan view illustrating an outer surface of the tape-type disposable diaper in a state where the diaper is spread.

FIG. 3 is a cross-sectional view taken along line 6-6 of FIG. 1.

FIG. 4 is a cross-sectional view taken along line 7-7 in FIG. 1.

FIG. 5(a) is a cross-sectional view taken along line 8-8 in FIG. 1, and FIG. 5(b) is a cross-sectional view taken along line 9-9 in FIG. 1.

FIG. 6 is a cross-sectional view taken along line 5-5 in FIG. 1.

FIG. 7 is an explanatory view of a sheet material forming a target sheet, in which FIG. 7(a) is a conceptual perspective view, FIG. 7(b) is a view from an X-direction, and FIG. 7(c) is a view from a Y-direction.

FIG. 8 is a schematic view illustrating a main part of a manufacturing apparatus.

FIG. 9 is a schematic view illustrating the main part of the manufacturing apparatus.

FIG. 10 is a photograph illustrating an imaging result by an image sensor.

DESCRIPTION OF EMBODIMENTS

FIGS. 1 to 6 illustrate an example of a tape-type disposable diaper. In the figures, a reference character X indicates a maximum width of the diaper excluding a connecting tape, a reference character L indicates a maximum length of the diaper, and a dotted pattern portion in cross-sectional views indicates a hot melt adhesive as bonding means that bonds respective constituent members located on a front surface side and a back surface side thereof. The hot melt adhesive can be applied by a known method such as slot application, continuous linear or dotted bead application, spiral or Z-shaped spray application, or pattern application (transfer of the hot melt adhesive in a letterpress method). Instead or additionally, in a fixing part of an elastic member, the hot melt adhesive can be applied to an outer peripheral surface of the elastic member, and the elastic member can be fixed to an adjacent member. Examples of the hot melt adhesive include EVA (ethylene-vinyl acetate)-based, adhesion rubber-based (elastomer-based), polyolefin-based, and polyester/polyamide-based adhesives, and can be used without any particular limitation. As bonding means that bonds respective components, it is possible to use means by material welding such as heat sealing or ultrasonic sealing.

This tape-type disposable diaper has a crotch portion M including a center in a front-back direction LD, a ventral side part F extending forward from a center in the front-back direction LD, and a dorsal side part B extending backward from the center in the front-back direction LD. In addition, this tape-type disposable diaper has an absorber 56 incorporated in a range including a crotch portion, a liquid pervious top sheet 30 disposed on the front surface side of the absorber 56, a liquid impervious sheet 11 that covers the back surface side of the absorber 56, and an outer nonwoven fabric 12 that covers the back surface side of the liquid impervious sheet and is included in an outer surface of a product.

Materials and characteristic parts of each part will be described below in order.

(Absorber)

The absorber 56 is a part that absorbs and retains excreted liquid, and can be formed of a fiber assembly. As this fiber assembly, in addition to those obtained by accumulating short fibers such as fluff pulp and synthetic fibers, it is possible to use a filament assembly obtained by opening a tow (fiber bundle) of synthetic fibers such as cellulose acetate as required. A fiber basis weight can be set to, for example, about 100 to 300 g/m$^2$ in the case of accumulating fluff pulp or short fibers, and can be set to, for example, about 30 to 120 g/m$^2$ in the case of the filament assembly. The fineness of the synthetic fiber is, for example, 1 to 16 dtex, preferably 1 to 10 dtex, and more preferably 1 to 5 dtex. In the case of the filament assembly, the filament may be non-crimped fiber, and is preferably crimped fiber. The crimp degree of the crimped fibers can be, for example, about 5 to 75, preferably 10 to 50, and more preferably about 15 to 50 per 2.54 cm. In addition, crimped fibers that are uniformly crimped can be used.

(Super Absorbent Polymer Particles)

The absorber 56 may contain super absorbent polymer particles in a part or all thereof. The super absorbent polymer particles include "powder" in addition to "particles". As the super absorbent polymer particles, those used for this type of absorbent articles can be used on an as-is basis. A particle size of the super absorbent polymer particle is not particularly limited. For example, it is desirable to use those in which when sieving (shaking for 5 minutes) using a standard sieve of 500 μm (JIS Z8801-1:2006) and sieving (shaking for 5 minutes) using a standard sieve (JIS Z8801-1:2006) of 180 μm for particles falling under the former sieve are performed, a ratio of particles remaining on the standard sieve of 500 μm is 30% by weight or less, and a ratio of particles remaining on the standard sieve of 180 μm is 60% by weight or more.

The material of the super absorbent polymer particles can be used without particular limitation, but the material having the water absorption capacity of 40 g/g or more is suitable. As the super absorbent polymer particles, starch-based, cellulose-based, and synthetic polymer-based, and starch-polyacrylate (salt) graft copolymers, saponified starch-acrylonitrile copolymers, sodium carboxymethyl cellulose crosslinked products, polyacrylate (salt) polymers, and the like can be used. As the shape of the super absorbent polymer particles, the shapes of particulate materials which are usually used are suitable, but other shapes can also be used.

The super absorbent polymer particles having a water absorption speed of 70 seconds or less, particularly 40 seconds or less, are suitably used. If the water absorption speed is too slow, back-flow, in which the liquid fed into the absorber 56 returns to the outside of the absorber 56, is likely to occur.

In addition, the super absorbent polymer particles having the gel strength of 1,000 Pa or more are preferably used. Thereby, even when the absorber 56 is bulky, it is possible to effectively suppress stickiness after liquid absorption.

The basis weight of the super absorbent polymer particles can be appropriately determined according to the absorption amount required for the use of the absorber 56. Therefore, although it cannot be said unconditionally, in a normal case, the basis weight can be 50 to 350 g/m$^2$.

(Wrapping Sheet)

To prevent super absorbent polymer particles from leaking out, or to improve a shape maintaining property of the absorber 56, the absorber 56 can be incorporated as an absorbent element 50 wrapped with the wrapping sheet 58. As the wrapping sheet 58, tissue paper, particularly crepe paper, a nonwoven fabric, a polyethylene laminated nonwoven fabric, a sheet with small holes, and the like can be used. However, it is desirable that the wrapping sheet be a sheet through which the super absorbent polymer particles do not pass. When a nonwoven fabric is used instead of crepe paper, a hydrophilic SMMS (Spunbonded/Melt blown/Melt blown/Spunbonded) nonwoven fabric is particularly suitable, and polypropylene, polyethylene/polypropylene, etc. can be used as a material. It is desirable that the basis weight of the fiber is 5 to 40 g/m$^2$, desirably 10 to 30 g/m$^2$.

The wrapping sheet 58 may have a structure in which one sheet wraps the entire absorber 56 as illustrated in FIG. 3, or the entire absorber 56 may be wrapped with a plurality of sheets (two upper and lower sheets). The wrapping sheet 58 may be omitted.

(Top Sheet)

The top sheet 30 has a liquid pervious property. For example, it is possible to use a perforated or non-perforated nonwoven fabric, a porous plastic sheet, etc.

The top sheet 30 extends from a front end to a back end of the product in the front-back direction, and extends laterally from the absorber 56 in the width direction WD. However, for example, when starting points of rising gathers 60 described later are located on center sides of side edges of the absorber 56 in the width direction, appropriate deformation such as making the width of the top sheet 30 shorter than the maximum width of the absorber 56 can be made as necessary.

(Intermediate Sheet)

To prevent back-flow of the liquid permeating the top sheet 30, it is possible to provide an intermediate sheet (also referred to as "second sheet") 40 on the back surface side of the top sheet 30. The intermediate sheet 40 can be omitted.

As the intermediate sheet 40, various nonwoven fabrics can be preferably used, and a bulky air through nonwoven fabric can be particularly preferably used. It is preferable to use a composite fiber having a core-sheath structure for the air through nonwoven fabric. In this case, a resin used for the core may be polypropylene (PP), and is preferably polyester (PET) having high rigidity. A basis weight is preferably 17 to 80 g/m$^2$, more preferably 25 to 60 g/m$^2$. A thickness of a raw material fiber of the nonwoven fabric is preferably 2.0 to 10 dtex. In order to make the nonwoven fabric bulky, it is preferable to use eccentric fibers having no core in the center, hollow fibers, or eccentric and hollow fibers as mixed fibers of all or some of raw material fibers.

Although the intermediate sheet 40 in the illustrated example is shorter than the width of the absorber 56 and disposed at the center portion, it may be provided over the maximum width. Further, the intermediate sheet 40 may be provided over the maximum length of the diaper, or may be provided only at an intermediate part including an excretion position as in the illustrated example.

(Liquid Impervious Sheet)

The liquid impervious sheet 11 is not particularly limited, and preferably has moisture permeability. As the liquid impervious sheet 11, for example, a microporous sheet can be preferably used which is obtained by kneading a polyolefin-based resin such as polyethylene or polypropylene and an inorganic filler, forming a sheet with the kneaded materials and monoaxially or biaxially stretching the sheet. Further, as the liquid impervious sheet 11, it is possible to use a sheet containing a nonwoven fabric as a base material and having enhanced waterproofness.

It is desirable that the liquid impervious sheet 11 extends in the front-back direction LD and the width direction WD in the same or wider range as or than that of the absorber 56. However, in a case where other water blocking means are present, etc., as necessary, it is possible to adopt a structure in which the liquid impervious sheet 11 does not cover an end portion of the absorber 56 in the front-back direction LD and the width direction WD.

(Outer Nonwoven Fabric)

The outer nonwoven fabric 12 covers the entire back surface side of the liquid impervious sheet 11 and makes the outer surface of the product look like a cloth. In addition to using a single piece of nonwoven fabric, it is also possible to use multiple nonwoven fabrics in layers. In the latter case, it is preferable that the nonwoven fabrics are attached to each other with a hot melt adhesive or the like. When a nonwoven fabric is used, it is preferable that a constituent fiber of the nonwoven fabric has a fineness of 1.6 to 2.3 dtex, a basis weight of 15 to 25 g/m$^2$, and a thickness of 0.3 to 0.8 mm.

(Rising Gather)

In order to prevent excrement that moves laterally on the top sheet 30 and prevent so-called side leakage, the rising gathers 60 standing up to the skin side of the wearer are preferably provided on both sides of the surface in the width direction WD. Naturally, the rising gathers 60 can be omitted.

When the rising gathers 60 are adopted, a structure thereof is not particularly limited, and any known structure can be adopted. Each of the rising gathers 60 of the illustrated example includes a gather sheet 62 that is substantially continuous in the width direction WD and an elongated gather elastic member 63 fixed to the gather sheet 62 in a stretched state along the front-back direction LD. As this gather sheet 62, a water repellent nonwoven fabric can be used, and rubber thread or the like can be used as the gather elastic member 63. As illustrated in FIGS. 1 and 2, a plurality of the elastic members may be provided on each side, or only one elastic member may be provided on each side.

The inner surface of the gather sheet 62 has a joint start point in the width direction WD on the side portion of the top sheet 30, and a part from the joint start point to an outer side in the width direction is bonded to an inner surface of each side flap portion SF, that is, a side portion of the liquid impervious sheet 11 and a side portion of the outer nonwoven fabric 12 located on the outer side thereof in the width direction in the illustrated example by a hot melt adhesive, etc.

In the circumference of the leg, the inside in the width direction from the joint start point of each rising gather 60 is fixed on the top sheet 30 at both ends of the product in the front-back direction. However, the portion therebetween is a non-fixed free portion, and this free point is erected by contraction force of the elastic member 63 and comes into close contact with a body surface.

(End Flap Portion and Side Flap Portion)

The tape-type disposable diaper of the illustrated example includes a pair of end flap portions EF that extends to the front side and the back side of the absorber 56, and does not have the absorber 56, and a pair of side flap portions SF that extends laterally beyond both side edges of the absorber 56 and does not have the absorber 56. The side flap portions SF may be made of a material (outer nonwoven fabric 12, etc.) continuous from a portion having the absorber 56 as in the illustrated example, or may be formed by attaching another material.

(Flat Gather)

Side elastic members 64 made of an elongated elastic member such as rubber thread are fixed to the respective side flap portions SF in an extended state along the front-back direction LD. In this way, around-leg parts of the respective side flap portions SF are configured as flat gathers. The side elastic members 64 may be provided between the gather sheet 62 and the liquid impervious sheet 11 on the outer side in the width direction near the joint start point in the bonded portion of the gather sheet 62 as in the illustrated example, or may be provided between the liquid impervious sheet 11 and the outer nonwoven fabric 12 in the side flap portions SF. As in the illustrated example, a plurality of side elastic members 64 may be provided on each side, or only one side elastic member 64 may be provided on each side.

The flat gather is a part where the contraction force of the side elastic members 64 acts (the part where the side elastic members 64 are illustrated in the figure). Therefore, in addition to a mode in which the side elastic members 64 are present only in a part of the flat gather, the following structure is included. In this structure, even though the side elastic members 64 are present on the front side, back side, or both sides of the flat gather, the side elastic members are finely cut at one place or a plurality of places in a part other than a site of the flat gather, are not fixed to sheets interposing the side elastic members 64 therebetween, or correspond to both the cases, so that the contraction force does not act on a site other than the flat gather (substantially equivalent to not providing the elastic members), and the contraction force of the side elastic members 64 acts only on the site of the flat gather.

(Wing Part)

In the tape-type disposable diaper, the dorsal side part B has wing parts WP extending outward from the crotch portion M in the width direction WD. Similarly, the ventral side part F has wing parts WP extending outward from the crotch portion M in the width direction WD. These wing parts WP can be formed by members different from the other parts. However, in the structure having the side flap portions SF as in the illustrated example, when a middle in the front-back direction LD in each of side portions of the side flap portions SF is cut to form a concave edge 70 from a side edge of the crotch portion M to a lower edge 71 of the wing part, and as a result the wing part WP is formed, it is easy to manufacture, and thus it is preferable.

(Connecting Tape)

As illustrated in FIGS. 1, 2, and 6, connecting tapes 80 to be detachably connected to the outer surface of the ventral side part F are provided in the wing parts WP in the dorsal side part B. When the diaper is worn, the connecting tapes 80 are turned from both sides of the waist to the outer surface of the ventral side part F, and connecting portions 83 of the connecting tapes 80 can be connected to proper positions on the outer surface of the ventral side part F.

As illustrated in FIG. 6, each of the connecting tapes 80 has a base portion 81 fixed to the wing part WP, a sheet base material 80S forming a main unit section 82 extending from the base portion 81, and the connecting portion 83 for the ventral side part F provided at an intermediate portion of the main unit section 82 in the width direction WD in the sheet base material 80S. In the main unit section 82, a part on the base portion 81 side of the connecting portion 83 is a non-connecting portion 84 not connected to the ventral side part F, and a part on the opposite side is a tab part 85. The non-connecting portion 84 and the tab part 85 include only the sheet base material 80S forming the main unit section 82.

As the connecting portion 83, a hook material (male member) of a mechanical fastener (hook and loop fastener) may be provided, or an adhesive layer may be provided. The hook material has a plurality of engagement projections on a connecting surface thereof, and the engagement projection has a (A) check mark shape, a (B) J shape, a (C) mushroom shape, a (D) T shape, and a (E) double J shape (a shape bonded back to back of a J shape), but may have any shape.

Further, as the sheet base material 80S forming from the base portion 81 to the main unit section 82, a nonwoven fabric, a plastic film, a polyethylene laminated nonwoven fabric, paper, or a composite material thereof can be used. It is preferable to use a spunbonded nonwoven fabric, an air through nonwoven fabric, or a spun lace nonwoven fabric having a fineness of 1.0 to 3.5 dtex, a basis weight of 60 to 100 g/m$^2$, and a thickness of 1 mm or less.

Even though the connecting portion 83 of the illustrated example is provided on the sheet base material 80S of the connecting tape 80 protruding from the wing part WP, the connecting portion 83 may be provided directly on the wing part WP.

(Target Sheet)

A target sheet 20 is provided at a connecting position of the connecting tape 80 in the ventral side part F. A shape of the target sheet 20 can be any shape such as a rectangular shape as in the illustrated example. In the target sheet 20, as in the illustrated example, a sheet material for facilitating connection can be stuck to the outer surface of the ventral side part F using a hot melt adhesive, etc.

The sheet material for forming the target sheet 20 is not particularly limited. However, when the connecting portion 83 is a hook material, for example, it is possible to use a long-fiber nonwoven fabric in which fibers are partially welded to each other by ultrasonic welding of an intermittent pattern. In this case, the long-fiber nonwoven fabric is preferably a nonwoven fabric in which a constituent fiber has a fineness of 5 to 10 dtex, a basis weight of 20 to 40 g/m$^2$, and a thickness of 0.3 to 0.8 mm. In addition, as the nonwoven fabric, it is possible to use a stacked nonwoven fabric in which the same or different types of nonwoven fabric layers are stacked. In this case, the fineness, the basis weight, and the thickness are preferably within the above ranges.

In addition, when the connecting portion 83 is the hook material, as the sheet material 20S for forming the target sheet 20, as illustrated in FIG. 7, it is possible to use a sheet material in which a number of loop threads are provided on a surface of a base material made of a plastic film or a nonwoven fabric so that engagement projections of the hook material are entangled. The illustrated example is a composite sheet material 20S in which loop pile fiber yarns 26 are sewn on at least an outer surface of a base material 25. The loop pile fiber yarns 26 are projected on the outer surface of the base material 25, that is, on the outer surface side of the disposable diaper at intervals in a latitude direction, and the loop pile fiber yarns 26 are combined with each other on a back surface side (wearer side) of the base material 25 to form an intersecting row 27 of the loop pile fiber yarns 26.

On the other hand, when the connecting portion 83 is an adhesive layer, as the sheet material for forming the target sheet 20, it is possible to use a sheet material made of a plastic film having a smooth surface that has a high adhesiveness and is subjected to a peeling treatment on a surface thereof.

(Whiteness)

It is preferable that the whiteness of all corner portions 21 on at least one of the inner surface and the outer surface of the target sheet 20 is 80% or more. By using such a target sheet 20, a position of the target sheet 20 can be continuously detected on a production line by the following method.

That is, as illustrated in FIG. 8, after the target sheet 20 is stuck to an outer surface constituent member (outer nonwoven fabric 12 in the illustrated example) of the ventral side part F, light of a light source 91 is emitted from a side of the target sheet 20 having a surface whose whiteness is 80% or more, transmitted light transmitted to the opposite surface is detected by a photodetector such as an image sensor 92, at least all corners of the target sheet 20 are detected based on a difference in light transmittance between a part having the target sheet 20 and a part not having the target sheet 20, and a sticking defect of the target sheet 20 is detected depending on whether or not the target sheet 20 recognized based on a detection result is normal. Here, when the whiteness of all the corner portions 21 on at least one of the inner surface and the outer surface of the target sheet 20 is 80% or more, light transmittance of all corner portions 21 of the target sheet 20 is sufficiently reduced, and a difference in light transmittance between at least all the corners of the target sheet 20 and an outer part thereof increases. Accordingly, at least all the corners of the target sheet 20 (that is, a minimum element for recognizing the dimensions and shape of the target sheet 20) are easier to detect. This method utilizes the fact that the light transmittance is lower than that of the surroundings since a part having high whiteness is a part that reflects light of all wavelengths. Since most of members of a disposable wear article (for example, top sheet, intermediate sheet, liquid impervious sheet, and outer sheet) are thin, are non-colored (white or milky white) in many cases, and have a light transmission property, the target sheet 20 can be detected by such a transmitted light detection method. In particular, by increasing the whiteness of the target sheet 20, an influence of the wavelength of light is reduced, so that restrictions on the light source 91 are reduced, and an influence of colors of the members other than the target sheet 20 is reduced.

As will be described later, for example, when the transmitted light is imaged by the image sensor 92 facing a part including the target sheet 20, as illustrated in FIG. 10(a), at least all the corner portions 21 of the target sheet 20 appear more distinctly blacker than the outer part thereof. Thus, by recognizing this black part as an image, at least all the corners of the target sheet 20 can be detected. Then, depending on whether the target sheet 20 recognized based on this detection result (for example, positions of the corners) is normal or not, it is possible to detect sticking defects such as curling of the corner portions 21 of the target sheet 20, misalignment of a sticking position, and deviation of the cutting dimension when the target sheet 20 is cut on the production line. On the other hand, in the case of a conventional general target sheet 20 having a whiteness of less than 65%, as illustrated in FIG. 10(*b*), a difference in shade between the part having the target sheet 20 and the other part is small, and detection by image recognition is difficult.

When only detection of the target sheet 20 is emphasized, it is best to increase the whiteness. However, when the whiteness of the target sheet 20 is excessively high, in a case where displays 22 and 23 seen through the outer surface of the target sheet 20 are printed on a part that overlaps the inside of the target sheet 20, the displays 22 and 23 may be difficult to see. Therefore, in such a case, the whiteness of the target sheet 20 is preferably 80 to 90%.

For example, in many conventional connectable disposable wear articles, the target display 22 such as a scale or a logo is printed on the target sheet 20, and the graphic display 23 such as a pattern or a character is printed around the target sheet 20. In this case, it is natural that printing on a plurality of members increases the cost. On the other hand, when a sheet having a first part overlapping the inside of the target sheet 20 and a second part extending around the first part (for example, the liquid impervious sheet 11 in the illustrated example) is used as a printing sheet, printing of the target display 22 and printing of other displays (for example, the graphic display 23) are integrated on this one print sheet, and the target display 22 is made to be seen through from the outer surface of the target sheet 20 without printing on the target sheet 20, the cost is significantly reduced. However, in this case, when the whiteness of the target sheet 20 is excessively high, the target display 22 may be difficult to see. Therefore, the whiteness of the target sheet 20 is preferably 90% or less as described above. Note that it is preferable that the target sheet 20 does not have printing (that is, plain) in this way. However, as long as the whiteness of all the corner portions 21 of the target sheet 20 is 80% or more, the target sheet 20 may have printing. In this case, the target sheet 20 does not have a register mark. However, the target sheet 20 may have a print that does not become or can become a register mark.

In the surface of the target sheet 20 having the corner portions 21 whose whiteness is 80% or more, it is preferable that the whiteness of not only the corner portions 21 but also a part of an edge portion continuous over the adjacent corner portions 21 or an entire peripheral edge portion is 80% or more since edges 20*e* of the target sheet 20 can be detected as described later. Naturally, the whiteness may be 80% or more on the entire surface of the target sheet 20 having the corner portions 21 whose whiteness is 80% or more.

The surface of the target sheet 20 having the corner portions 21 whose whiteness is 80% or more may be either the inner surface or the outer surface, or both the surfaces (many target sheets 20 such as nonwoven fabrics have almost the same whiteness on the inner surface and outer surface). During detection, it is sufficient to irradiate a side of the target sheet 20 having a surface whose whiteness is 80% or more with light and detect light on the opposite side. Further, positions of the light source 91 and the photodetector (image sensor 92 in the illustrated example) are not limited during detection. However, it is preferable that the surface of the target sheet 20 whose whiteness is 80% or more is set to the inner surface, and after the inner surface of the target sheet 20 is stuck to the outer surface constituent member (outer nonwoven fabric 12 in the illustrated example) of the ventral side part F during manufacturing as illustrated in FIG. 8, the surface opposite to the target sheet 20 side is irradiated with light of the light source 91, and transmitted light transmitted through the surface on the target sheet 20 side is detected by the photodetector (image sensor 92 in the illustrated example) since a contour of the target sheet 20 can be detected more clearly.

Depending on the material of the target sheet 20, it may be difficult to increase the whiteness. For example, as the connecting portion 83, a hook material of a mechanical fastener is generally used. In this case, it is preferable to use a nonwoven fabric as the target sheet 20 since a soft touch is obtained. When the target sheet 20 is a nonwoven fabric, the density can be increased in order to increase the whiteness. However, in this case, the hook material of the connecting portion 83 may not be easily entangled. Further, as will be described later, when the displays 22 and 23 seen through from the outer surface of the target sheet 20 are printed on the part that overlaps the inside of the target sheet 20, the displays 22 and 23 may be difficult to see through. Therefore, it is preferable to use a nonwoven fabric in which a constituent fiber has a fineness of 5 to 10 dtex, a basis weight of 20 to 40 g/m$^2$, and a thickness of 0.3 to 0.8 mm as the target sheet 20, and make up for the lack of whiteness by adding an appropriate amount of a white pigment such as titanium oxide. Even when the target sheet 20 is other than the nonwoven fabric, the whiteness can be kept within the above range by using a white pigment, etc. Further, the whiteness of the target sheet 20 may be set within the above range by using a dye or ink without using a white pigment. Naturally, when the whiteness of the material of the target sheet 20 is high, a pigment or dye may not be used.

The detection position of the target sheet 20 on the production line can be determined as appropriate. However, it is preferable that the number of members overlapping the target sheet 20 is small (that is, light is easily transmitted) in order to improve the detection accuracy. Therefore, in the case of the disposable diaper of the illustrated example, it is preferable to detect the target sheet 20 on the production line in a state where the target sheet 20 is merely attached to the outer surface of the outer nonwoven fabric 12 which is an outer surface constituent member (that is, only these two members) as illustrated in FIG. 8(*a*). In addition, although not illustrated, in the case of a disposable diaper not having the outer nonwoven fabric 12, it is preferable to detect the target sheet 20 on the production line in a state where the target sheet 20 is merely attached to the outer surface of the liquid impervious sheet 11 which is an outer surface constituent member (that is, only these two members). However, in this way, even though the shape and dimensions of the target sheet can be detected, misalignment of the sticking position of the target sheet may not be detected. That is, in the case of detecting misalignment of the sticking position of the target sheet 20, a register mark as a reference position is necessary in addition to the target sheet 20. Further, when this register mark is assigned to a member inside the outer surface constituent member, the target sheet 20 and the register mark need to be detected in a state where the inner member, the outer surface constituent member, and the target sheet 20 are stacked.

On the other hand, when a register mark is assigned to the member inside the outer surface constituent member, for example, the liquid impervious sheet 11, and as illustrated in FIG. 8(*b*), the target sheet 20 and the register mark are detected in a state where the liquid impervious sheet 11 is merely stuck to the inner surface of the outer nonwoven fabric 12 and the target sheet 20 is merely stuck to the outer surface thereof (that is, only these two members), it is possible to detect misalignment of the sticking position of the target sheet 20 according to a positional relationship between the register mark and the target sheet 20 recognized based on these detection results. As illustrated in FIG. 9(a), in a case where the target sheet 20 is stuck after the liquid impervious sheet 11 is stuck to the inner surface of the outer nonwoven fabric 12, by detecting the target sheet 20 on the downstream side of the sticking position of the target sheet 20, the shape and dimensions of the target sheet 20 and misalignment of the sticking position of the target sheet 20 may be detected at one time. As illustrated in FIG. 9(b), by modifying the example illustrated in FIG. 8(a) and detecting the target sheet 20 on the downstream side of the sticking position of the liquid impervious sheet 11 without performing detection in two steps, the shape and dimensions of the target sheet 20 and misalignment of the sticking position of the target sheet 20 may be detected at one time.

In these cases, the outer nonwoven fabric 12 preferably has a whiteness of 90% or less on one of the inner surface and the outer surface on the same side as the surface of the target sheet 20 whose whiteness is 80% or more. Similarly, the liquid impervious sheet 11 preferably has a whiteness of 90% or less on one of the inner surface and the outer surface on the same side as the surface of the target sheet 20 whose whiteness is 80% or more. Note that white arrows of FIG. 8 indicate a hot melt adhesive coating device for attaching the outer nonwoven fabric 12 and the target sheet 20 and a hot melt adhesive coating device for attaching the outer nonwoven fabric 12 and the liquid impervious sheet 11. In the illustrated example, the target sheet 20 is supplied as a continuous belt shaped body 20T, cut by a slip cutter device 99, and then stuck to the outer nonwoven fabric 12 at predetermined intervals.

The light source 91, the photodetector, and the method of detecting the sticking defect of the target sheet 20 based on the detection result thereof are not particularly limited. For example, when the light source 91 can illuminate either a front or back surface of a stacked body of the outer surface constituent member of the ventral side part F and the target sheet 20, the light source 91 may directly face the surface or indirectly illuminate the surface. The light source 91 may emit light which is detectable by the photodetector and includes a part or all of light in the visible wavelength range (lower limit 360 to 400 nm, upper limit 760 to 830 nm). In particular, light with a measurement wavelength of whiteness (effective wavelength 457 nm, half width 44 nm) is preferable, and for example, white light described later is preferable. As the photodetector, for example, the image sensor 92, which detects light on the surface opposite to the light source 91 in the stacked body of the outer surface constituent member of the ventral side part F and the target sheet 20, is suitable. A type of the image sensor 92 is not particularly limited. However, as illustrated in FIG. 8, it is possible to use an image sensor including a full-color camera 92a equipped with an image sensor such as CCD (Charge Coupled Device) or CMOS (Complementary Metal Oxide Semiconductor), and a controller 92b that performs, for an imaging result of this camera 92a, image processing such as conversion to a grayscale image, detection of the edges 20e, etc., and defect detection based thereon.

When such an image sensor 92 is used, the target sheet 20 can be detected by, for example, the following processing. That is, the imaging result of the full-color camera 92a is converted into a grayscale image by the controller 92b. A monochrome camera 92a may be used without performing the conversion processing from the color image to the grayscale image. As necessary, contrast adjustment, contour line enhancement processing, contour line smoothing processing, etc. can be performed by image processing for a color image or a grayscale image. In the acquired grayscale image, the target sheet 20 appears clearly blacker than an outer part thereof. Thus, the controller 92b detects, for example, all the edges 20e of the target sheet 20 by recognizing a part of the grayscale image having a predetermined gradation or less as an image. Naturally, a detection target may not be all the edges 20e of the target sheet 20, and a defect can be detected when at least all corners can be detected. By performing image recognition using a grayscale image in this way, simpler and faster detection processing can be performed. Further, since the whiteness of the target sheet 20 is used, even when a grayscale image is used, there is an advantage that a clearer difference is generated and an influence on the detection accuracy is small. Naturally, a similar detection method can be performed by using another known image sensor 92.

As an example, when the grayscale image has 256 levels of gradation and the gradation of the part of the target sheet 20 is approximately 190-level gradation or less, the edges 20e of the target sheet 20 can be detected using this gradation as a boundary. A boundary value of this gradation can be appropriately determined according to conditions such as the intensity of the light source 91, the sensitivity and gain of the camera 92a, etc. However, it is desirable to install and adjust the light source 91 and the camera 92a so that a difference in gradation between the part of the target sheet 20 and the other parts is 30 or more, more preferably 35 or more.

Then, the controller 92b can determine whether or not the target sheet 20 recognized based on the detected position, pitch, number, angle, etc. of the edges 20e is within a preset normal range, and detect sticking defects such as curling of the corner portions 21 of the target sheet 20, and deviation of the cutting dimension when the target sheet 20 is cut on the production line. Further, as described above, when the register mark serving as a reference position of the target sheet 20 is assigned to the member inside the outer surface constituent member, the controller 92b in the same or different image sensor 92 detects not only the edges 20e of the target sheet 20 but also the register mark as a reference position by image recognition. In this way, the controller 92b can also detect the misalignment of the sticking position of the target sheet 20 according to a positional relationship between the target sheet 20 recognized based on the detected position, pitch, number, angle, etc. of the edges 20e and the detected register mark.

The light source 91 and the photodetector may be disposed in a straight line in a substantially orthogonal direction with respect to the stacked body of the outer surface constituent member and the target sheet 20, or disposed so that an illumination direction of the light source 91 and a detection direction of the photodetector (direction of the camera 92a) intersect in the vicinity of the stacked body by slightly tilting either or both of the light source 91 and the photodetector.

(Nonwoven Fabric)

As the nonwoven fabric in the above description, a known nonwoven fabric can be appropriately used depending on the part and purpose. As the constituent fibers of the nonwoven fabric, for example, synthetic fibers (including not only single component fibers but also conjugate fibers such as core sheath type fiber) such as polyolefin-based such as polyethylene or polypropylene, polyester type, and polyamide type, regenerated fibers such as rayon and cupra, and natural fibers such as cotton can be selected without limitation, and a combination thereof can be used. In order to increase flexibility of the nonwoven fabric, it is preferable that the constituent fibers are crimped fibers. Further, the constituent fibers of the nonwoven fabric may be hydrophilic fibers (including fibers made hydrophilic by a hydrophilic agent), or hydrophobic fibers or water repellent fibers (including fibers made water repellent by a water repellent agent). Further, in general, depending on the length of the fiber, the sheet forming method, the fiber bonding method, and the stacked structure, nonwoven fabrics are classified into short fiber nonwoven fabric, long fiber nonwoven fabric, spunbonded nonwoven fabric, melt blown nonwoven fabric, spun lace nonwoven fabric, thermal bond (air through) nonwoven fabric, needle punch nonwoven fabric, point bond nonwoven fabric, stacked nonwoven fabric (SMS (Spunbonded/Melt blown/Spunbonded) nonwoven fabric, SMMS nonwoven fabric, etc. in which a melt blown layer is interposed between spunbonded layers), etc. Any of these nonwoven fabrics can be used.

For the liquid impervious sheet 11, a moisture-permeable polyethylene film containing calcium carbonate particles was used. In addition, the liquid impervious sheet 11 had a basis weight of 17 g/m$^2$ and a thickness of 20 μm, and had a whiteness of 78.2% on the outer surface and 83.7% on the inner surface. Further, a sheet having a register mark serving as a reference position of the target sheet 20 printed was used as the liquid impervious sheet 11.

Test results are shown in Table 1. For target sheets of No. 1, No. 3 and No. 4, it was possible to detect defects by both the upstream and downstream image sensors. On the other hand, for a target sheet of No. 2, it was not be possible to detect a defect by either the upstream side or downstream side image sensor in some cases. From these results, it was found that when the whiteness of the target sheet is 80% or more, the detectability of the target sheet by the transmitted light detection method is improved.

TABLE 1

|  | No. 1 | No. 2 | No. 3 | No. 4 |
| --- | --- | --- | --- | --- |
| Fineness (dtex) | 7 | 7 | 7 | 7 |
| Basis weight (g/m$^2$) | 30 | 35 | 35 | 35 |
| Thickness (mm) | 0.4 | 0.4 | 0.4 | 0.4 |
| Material | Polypropylene | Polypropylene | Polypropylene | Polypropylene |
| Manufacturing method | Spunbonded | Spunbonded | Spunbonded | Spunbonded |
| Whiteness (%) on outer surface | 83.9 | 71.9 | 81.2 | 86.1 |
| Whiteness (%) on inner surface | 84.0 | 71.8 | 81.2 | 85.7 |
| Detection possibility | Possible | Impossible | Possible | Possible |

<Effect Confirmation Test>

Each target sheet shown in Table 1 was prepared, and a defect detection test for the target sheet was performed on the same production line as that illustrated in FIG. 8(b). In the test, a situation where the corner portions of the target sheet are curled, a situation where the cutting dimension of the target sheet 20 is deviated, a situation where the sticking position of the target sheet is misaligned, and a normal situation were artificially created to evaluate whether the defect can be detected.

For the image sensor 92 on the upstream side, XG-7500 (controller 92b), XG-0035 (camera 92a), and CV-L6 (camera lens) manufactured by KEYENCE CORPORATION were used. For the light source 91 to be combined with the image sensor 92 on the upstream side, two white flat illuminations LF1F-B4-2D3 manufactured by IDEC Corporation were used. The image sensor 92 on the upstream side detected curling of the corner portions 21 of the target sheet 20 and deviation of the cutting dimension of the target sheet 20.

For the image sensor 92 on the downstream side, XG-7000 (controller 92b), XG-0035 (camera 92a), and CV-L3 (camera lens) manufactured by KEYENCE CORPORATION were used. For the light source 91 to be combined with the image sensor 92 on the downstream side, four white LED (light emitting diode) illuminations LF1B-ND4P-2THWW2 manufactured by IDEC Corporation were used. The image sensor 92 on the downstream side detected misalignment of the sticking position of the target sheet 20.

The outer nonwoven fabric 12 is made of polypropylene fiber having a fineness of 2.0 dtex, and a spunbonded nonwoven fabric having a basis weight of 20 g/m$^2$ and a thickness of 0.5 mm was used. This spunbonded nonwoven fabric contained titanium oxide, and the whiteness was 83.5% on both the outer and inner surfaces.

<Description of Terms Used Herein>

The following terms in the description have the following meanings unless otherwise specified in the specification.

"Front-back direction" means a direction (longitudinal direction) indicated by the reference character LD in the figure, "width direction" means a direction (right-left direction) indicated by WD in the figure, and the front-back direction and the width direction are orthogonal to each other.

"Spread state" means a flatly spread state without contraction or slack.

"Stretch rate" means the value when the natural length is taken as 100%. For example, a stretch rate of 200% is synonymous with a stretch magnification of 2 times.

"Gel strength" is measured as follows: 1.0 g of super absorbent polymer is added to 49.0 g of artificial urine (urea: 2 wt %, sodium chloride: 0.8 wt %, calcium chloride dihydrate: 0.03 wt %, magnesium sulfate heptahydrate: 0.08 wt %, and ion exchanged water: 97.09 wt %), and stirred with a stirrer. The resulting gel is left for three hours in a thermohygrostat bath at 40° C.×60% RH and then cooled to room temperature. The gel strength of the gel is measured with a curd meter (Curdmeter-MAX ME-500, manufactured by I.techno Engineering).

"Basis weight" is measured as follows. After the sample or test piece is preliminary dried, it is allowed to stand in a test room or apparatus under normal conditions (the test location is at a temperature: 23±1° C., relative humidity: 50±2%) until the constant mass. The preliminary drying is to make the sample or test piece be constant mass in an environment of a temperature of 100° C. Note that the fibers of an official moisture regain of 0.0% do not need preliminary drying. From a test piece having a constant weight, a sample having a dimension of 100 mm×100 mm is cut out using a template for sampling (100 mm×100 mm). The sample is weighed and the weight is multiplied by 100 into the weight per one square meter. The resulting value is defined as the basis weight.

"Thickness" is automatically measured under the conditions of a load of 0.098 N/cm² in a pressurized area of 2 cm² using an automatic thickness measuring device (KES-G5 handy compression tester).

"Water absorption capacity" is measured in accordance with JIS K7223-1996 "Testing method for water absorption capacity of super absorbent resins".

"Water absorption speed" is the "time that elapses before the end point" measured in accordance with JIS K7224-1996 "Testing method for water absorption speed of super absorbent polymers" has been carried out using 2 g of superabsorbent polymer and 50 g of physiological saline solution.

When environmental conditions in tests and measurements are not described, the tests and measurements shall be carried out in a test room or apparatus under normal conditions (the test location is at a temperature: 23±1° C., relative humidity: 50±2%).

The dimension of each part means the dimension in the unfolded state, not the natural length state, unless otherwise specified.

Industrial Applicability

The invention is applicable to the connectable disposable wear article such as the tape-type disposable diaper of the above example.

REFERENCE SIGNS LIST

11 LIQUID IMPERVIOUS SHEET
12 OUTER NONWOVEN FABRIC
80 CONNECTING TAPE
83 CONNECTING PORTION
82 MAIN UNIT SECTION
81 BASE PORTION
20 TARGET SHEET
21 CORNER PORTION
20S SHEET MATERIAL
22, 23 DISPLAY
22 TARGET DISPLAY
23 GRAPHIC DISPLAY
30 TOP SHEET
40 INTERMEDIATE SHEET
50 ABSORBENT ELEMENT
56 ABSORBER
58 WRAPPING SHEET
60 RISING GATHER
62 GATHER SHEET
64 SIDE ELASTIC MEMBER
70 CONCAVE EDGE
71 LOWER EDGE OF WING PART
91 LIGHT SOURCE
92 IMAGE SENSOR
92a CAMERA
92b CONTROLLER
20e EDGE
B DORSAL SIDE PART
F VENTRAL SIDE PART
LD FRONT-BACK DIRECTION
M CROTCH PORTION
SF SIDE FLAP PORTION
WD WIDTH DIRECTION
WP WING PART

The invention claimed is:

1. A method of detecting a sticking defect of a target sheet in a manufacture of a connectable disposable wear article, the connectable disposable wear article comprising:
  a crotch portion including a center in a front-back direction, a ventral side part extending forward from the center in the front-back direction, and a dorsal side part extending backward from the center in the front-back direction;
  connecting portions to be detachably connected to an outer surface of the ventral side part and that are provided on both side portions of the dorsal side part, each of the connecting portions being a hook material of a mechanical fastener, and
  a target sheet to which the connecting portions are to be connected and which is provided on the outer surface of the ventral side part,
  wherein the target sheet is a nonwoven fabric of which constituent fibers have a fineness of 5 to 10 dtex, and
  wherein the target sheet further has a basis weight of 20 to 40 g/m², a thickness of 0.3 to 0.8 mm, contains a white pigment, and wherein a whiteness of all corner portions on at least one of an inner surface and an outer surface of the target sheet is 80% or more,
  the method comprising:
  sticking the target sheet to an outer surface constituent member of the ventral side part, irradiating the target sheet from its side having a surface whose whiteness of all corner portions is 80% or more with white light and detecting transmitted light transmitted to an opposite surface;
  detecting at least all corners of the target sheet based on a difference in light transmittance between a part having the target sheet and a part not having the target sheet; and
  detecting a sticking defect of the target sheet depending on whether or not the target sheet recognized based on a detection result is normal.

2. The method of detecting a sticking defect of a target sheet in a manufacture of a connectable disposable wear article according to claim 1, further comprising:
  imaging the transmitted light by an image sensor facing the opposite surface and acquiring a grayscale image; and
  detecting at least all corners of the target sheet by recognizing a part of an imaging result having a predetermined gradation or less as an image.

3. The method of detecting a sticking defect of a target sheet in a manufacture of a connectable disposable wear article according to claim 1, further comprising
  sticking the surface of the target sheet whose whiteness is 80% or more to the outer surface constituent member of the ventral side part, irradiating a surface opposite to a side of the target sheet with light and detecting transmitted light transmitted to a surface on the side of the target sheet.

* * * * *